United States Patent
Øelund et al.

(10) Patent No.: US 6,726,791 B1
(45) Date of Patent: Apr. 27, 2004

(54) METHOD FOR PRODUCING A LAYERED PRODUCT

(75) Inventors: Jakob Øelund, Copenhagen (DK); Jan Petersen, Silkeborg (DK); Jan Marcussen, Taastrup (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/403,013

(22) PCT Filed: Sep. 27, 1999

(86) PCT No.: PCT/DK99/00505

§ 371 (c)(1),
(2), (4) Date: Oct. 18, 1999

(87) PCT Pub. No.: WO00/18554

PCT Pub. Date: Apr. 6, 2000

(30) Foreign Application Priority Data

Sep. 25, 1998 (DK) .......................... 1998 01222

(51) Int. Cl.⁷ ...................... B29C 39/06; B29C 39/10
(52) U.S. Cl. ...................... 156/199; 156/245; 264/37.1; 264/255; 264/267; 264/157; 264/297.6; 264/511; 264/172.19
(58) Field of Search .................. 264/172.19, 171.13, 264/157, 271.1, 297.6, 297.7, 511, 251, 255, 267, 520; 156/245, 199, 301

(56) References Cited

U.S. PATENT DOCUMENTS

| | | | |
|---|---|---|---|
| 3,419,006 A | 12/1968 | King | 128/268 |
| 3,895,988 A | 7/1975 | Miller | 156/245 |
| 3,972,328 A | 8/1976 | Chen | 128/156 |
| 4,367,732 A | 1/1983 | Poulsen et al. | 128/156 |
| 4,379,016 A | 4/1983 | Stemmler et al. | 156/205 |
| 4,421,712 A | 12/1983 | Winstead | 264/551 |
| 4,538,603 A | 9/1985 | Pawelchak et al. | 128/156 |
| 4,543,099 A | 9/1985 | Bunnelle et al. | 604/385 A |
| 4,552,138 A | 11/1985 | Hofeditz et al. | 128/156 |
| 4,867,748 A | 9/1989 | Samuelsen | 604/336 |
| 5,051,259 A | 9/1991 | Olsen et al. | 424/443 |
| 5,250,043 A | * 10/1993 | Castellana et al. | 604/336 |
| 5,366,685 A | 11/1994 | Fujii et al. | 264/547 |
| 5,609,585 A | 3/1997 | Botten et al. | 604/332 |
| 5,643,187 A | 7/1997 | Naestoft et al. | 602/43 |
| 5,714,225 A | 2/1998 | Hansen et al. | 428/114 |
| 6,149,614 A | * 11/2000 | Dunshee et al. | 602/57 |

FOREIGN PATENT DOCUMENTS

| | | |
|---|---|---|
| EP | 32 03 992 | 8/1983 |
| EP | 0 272 149 | 6/1988 |
| EP | 0 415 183 | 3/1991 |
| EP | 0 573 708 | 12/1993 |
| EP | 0 749 707 | 12/1996 |
| EP | 0 818 187 | 1/1998 |
| GB | 1 280 631 | 7/1972 |
| GB | 1 586 182 | 3/1981 |
| WO | WO88/06894 | 9/1988 |

OTHER PUBLICATIONS

Handbook of Common Polymers, 1971, p. 8.*

* cited by examiner

Primary Examiner—Edmund H. Lee
(74) Attorney, Agent, or Firm—Jacobson Holman PLLC

(57) ABSTRACT

A method for production of a layered product including at least two layers, a first primary layer and second mouldable layer, wherein a continuous supply of a primary layer material and a supply of mouldable material are provided and wherein the primary layer material and the mouldable material are combined in moulding cavities, wherein the moulding cavities are placed in an endless loop, and the mouldable material and the primary layer are combined by placing the mouldable material on the primary layer about and/or in communication with the moulding cavities.

15 Claims, 1 Drawing Sheet

METHOD FOR PRODUCING A LAYERED PRODUCT

BACKGROUND OF THE INVENTION

1. Field of the Invention

The present invention relates to a method for producing a layered product e.g., for use as a wound dressing or a semi-manufacture in the production of dressings, skin and wound care devices, fastening means for dressings, ostomy equipment, breast prostheses, wound drains and catheters for incontinence equipment, and for use in electrodes for application to the skin, a skin plate product producible by this method and being suitable for use as a wound dressing or a semi-manufacture in the production of dressings, skin and wound care devices, fastening means for dressings, ostomy equipment or the like, a layered product comprising a third component in the form of a discrete unit and an apparatus for carrying out the method.

2. Description of Related Art

From European Patent Application No.0 756 854 it is known to produce skin barrier wafers having a thin barrier layer of soft, pliant adhesive material with particles of one or more hydrocolloids dispersed therein, said wafers having a central zone and a relatively large outer zone surrounding that central zone. The material of the thin barrier layer in the outer zone has a generally uniform molecular orientation in radial directions which molecular orientation is caused by the barrier layer being produced by a method comprising injection and compression moulding, said method comprising the steps of:

depositing a mound of a soft, deformable skin barrier material onto a flexible first web extending along a horizontal plane and supported by a first platen;

locating a flexible second web above the first web and the mound, which second web is backed by a second platen positioned directly therein above; and thereafter reducing the spacing between said first and second platens and compressing said mound of skin barrier material to displace a major portion of said mound of skin barrier material radially outwardly in directions extending 360° about the original location of the deposit of said mound.

When placing a soft material as the second layer of plastic material on a sheet or web it should preferably be assured that the relaxation of the web and the forming of the plastic material is completed when the product leaves the form because complete relaxation of the web and the plastic material assures that the form of the product is maintained after the product has left the moulding cavity. One way to obtain this result is to leave the product in the mould for a longer time period. A problem with the method described in EP-A-0756854 is that increasing the time period of the product in the mould will seriously slow down the process and thus also reduce the amount of produced products. Another possibility is to increase the heat or the pressure in the compression step but increasing any of these parameters will increase the cost of the production.

European Patent Application No. 0 818 187 A1 discloses a process for making contoured dressings having a hydrocolloid-containing adhesive layer disposed between a stretchable backing layer and a planar release layer. The process comprises the step of providing a substantially continuous adhesive strip of a soft pliant adhesive material having at least one liquid absorbing hydrocolloid material dispersed therein and providing a substantially continuous supply of a backing web comprising a layer of stretchable material. The backing web is merged with the adhesive strip and the release layer to form a laminate in which said backing web has its layer of stretchable material in contact with one side of said adhesive strip and said release web is in contact with the strip's opposite side. Then pressure is applied to the laminate—without stretching said layer of stretchable material in planar directions—to contour the backing layer and the adhesive material of said laminate and the laminate is cut as it is being contoured to form discrete dressings of predetermined size and shape. The steps of merging the backing web with the adhesive strip, applying pressure and cutting of the laminate to form discrete dressings are all performed in a single operation in order to make the process simpler and faster compared to earlier published methods. A problem with this process might be the amount of adhesive material wasted by the cutting process if the total web is not utilised e.g., when producing dressings of curved and/or irregular contours.

EP Patent No. 573 708 discloses a method for making individual contoured wound dressings comprising:

providing a substantially continuous supply of a thin protective release covering and a substantially continuous strip of an adhesive material, where the strip of adhesive material has a predetermined thickness and malleable properties;

removably attaching the strip of adhesive material to the protective release covering while simultaneously contouring the adhesive material to a predetermined shape by merging and carrying a first laminate of the adhesive material and the protective release covering through a calibration and contouring station, providing a substantially continuous web of an adhesive carrier material; and merging—the adhesive layer to form a second laminate by applying the adhesive carrier layer to fully cover the exposed major surface of the adhesive layer while simultaneously applying pressure to the second laminate by carrying the second laminate to and through a laminating station.

Finally, the second laminate is cut into predetermined discrete sized and contoured individual wound dressings by carrying the second laminate to and through a cutting station in a predetermined registered and timed relationship.

When the adhesive material is provided as a strip it is impossible to avoid the loss of material during the cutting operation if the dressing is given a form diverting from e.g., rectangular or similar.

The German Patent Application DE 3016197 discloses a method for providing sections of elastic bands on a length of material for the production of baby pants or the like by discontinuously applying a corrugation and a liquid that solidifies into a state of elastic gum to the length of the material. Such method demands separate and accurate controlling of the application of liquid.

The object of the present invention is to provide a simple, cost efficient method for producing a layered product and a product producible by this method. The method eliminates the disadvantages known from the earlier described methods for producing layered products and furthermore the method according to the invention is sturdy, easy to control and it has a very high production rate.

BRIEF SUMMARY OF THE INVENTION

The present invention relates in a first aspect to a method for production of a layered product comprising at least two layers, a first primary layer and a second mouldable layer, wherein a continuous supply of a primary layer material and a supply of mouldable material, are provided and wherein the primary layer material and the mouldable material are combined in moulding cavities.

In a second aspect, the invention relates to a layered product comprising at least two layers where a first layer is constituted by a continuous and deformable sheet, a second layer is constituted by a mouldable material which material comprises a third component in the form of individual units forming a part of the surface of the mouldable material facing away from the deformable sheet.

In a third aspect, the invention relates to an apparatus for essentially continuous production of a layered product comprising at least two layers, a first primary layer and second mouldable layer, wherein a continuous supply of a primary layer material and a supply of mouldable material are provided and where the primary layer material and the mouldable material are combined in moulding cavities.

BRIEF DESCRIPTION OF THE DRAWING

The invention will now be described by way of example with reference to the accompanying FIG. 1 which is a diagrammatic drawing describing a schematic view of the process of this invention.

DETAILED DESCRIPTION OF THE INVENTION

Figure 1:
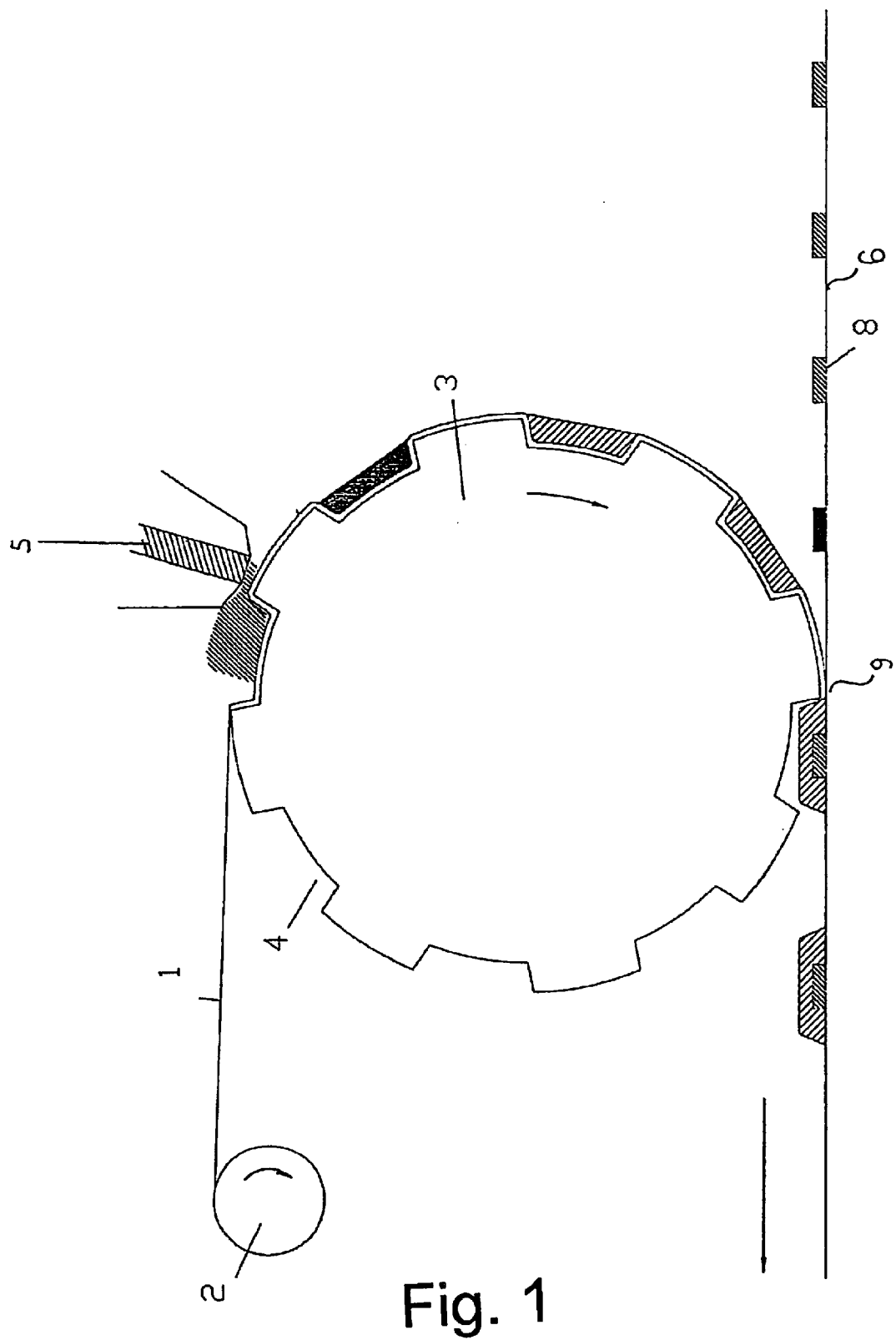

It has now been found that the above objects are fulfilled by the method of the invention.

Thus, the invention relates to a method for production of a layered product comprising at least two layers, a first primary layer and second mouldable layer, wherein a continuous supply of a primary layer material and a supply of mouldable material are provided and where the primary layer material and the mouldable material are combined in moulding cavities which method is characterised in providing moulding cavities placed in an endless loop, and combining the mouldable material and the primary layer by placing the mouldable material on the primary layer above and/or in communication with the moulding cavities. The endless loop can take the form of e.g., a roller provided with moulding cavities on the surface along the periphery. The moulding cavities can also be situated on a conveyor belt or similar suitable conveying means.

By this method it is possible to increase the number of produced units per hour and independently increase the time the units stay in the moulding cavity by increasing the length of the endless loop which opens for a considerable cooling before the product is removed from the mould ensuring better dimensional stability. Also it is possible to perform a completely continuous regulation of the process as the second layer of a plastic material can be added as a continuous stream and the endless loop can be led forward with a constant velocity. This increases the chances of finding an optimum for the process. Another result of using this method is that the hardened product has a random molecular orientation as the material is fed into the moulding cavity by a very low pressure, if any, as compared to the pressure used during ordinary injection moulding. Also it is very easy to change the form of the produced product, this can be done by changing moulds of the endless loop which can be in the form of, for example, a roller or an endless belt, and adjusting the amount of plastic material added to the moulding cavities in accordance with their volume.

It is preferred that the second mouldable material is provided as an essentially continuous coating with a varying thickness on the first primary layer. This may be achieved by providing the mouldable material at a rate corresponding essentially to the volume of the moulds. Surplus of the mouldable material can be removed from the cavity-free part of the surface and distributed into the next cavity e.g. by scraping or rolling.

A simple way to control the viscosity of the mouldable material is to use a thermoplastic material and regulate the temperature and thus the viscosity of the mouldable material.

Suitable vacuum can be used to secure the positioning of the first layer in the mould cavities. Thus in another embodiment of the invention a vacuum is created between the first layer and the walls of the mould cavity when contacting the first layer with the mould for improving the finish. This may be obtained by providing the walls of the moulding cavity with openings and evacuating the air from the intervening space. This will force the first layer into contact with the walls of the mould. If the moulds are porous e.g., when made out of a metal powder such as aluminum, the porous material itself can provide sufficient openings for evacuation of air.

In a preferred embodiment of the invention, the walls of the moulding cavities are heated to a temperature adequate to relax the material of the first layer partially of fully. Thus, less stress is built into the product., thereby improving the features of the final product during usage.

It is preferred to heat the walls of the moulding cavity to an adequate temperature, or to keep the mouldable material in a plasticized state, in order to reduce or eliminate built-in stress and to provide better surface finish. By reducing the built-in stress the features of the final product during usage are improved.

When applying the product, the presence of a release liner is often required. Thus in another embodiment of the invention a third component is combined with the laminate of the mouldable material and the primary layer together with the release liner.

Such a third component may be an adhesive having other properties than the mouldable material or it may be a purely absorbing material or a reservoir for administration of active ingredients.

The method is suitable for producing wound dressings or bandages. Especially when the product is wound dressings or bandages, the first layer may consist of one or more sheets or coatings e.g., the first layer may comprise a carrier layer and a cover layer wherein the carrier layer may e.g., be a part of the package of the finished product or simply an extra layer having no direct function in the final product. A carrier layer may comprise a predominantly deformable material e.g., polypropylene, polyethylene or treated paper. A cover layer covers the adhesive layer and forms a comfortable surface of the finished product when the product is in use.

The invention also relates to a method for production of dressings comprising at least two layers, a first primary layer and a second adhesive layer, wherein a continuous supply of a primary layer material and a supply of a mouldable adhesive material are provided and wherein the primary layer material and the mouldable adhesive material are combined and moulded in moulding cavities, which method is characterised in providing moulding cavities placed in an endless loop, combining the mouldable adhesive material and the primary layer material by placing the mouldable adhesive on the primary layer above and/or in communication with the moulding cavities, optionally removing all or some surplus of mouldable adhesive material, laminating a release liner on the adhesive and, at the same time or later in the process, contouring and cutting at least the primary layer or the release liner and the adhesive layer into individual, contoured dressings, removing the dressings from the moulding cavities and optionally separating the dressings into individual dressings and optionally packing the dressings.

Any surplus of mouldable adhesive material from one cavity or from the non-cavity area of the roller surface can be essentially removed by pressing or scraping using suitable means such as a roller, or a doctor or a scraping blade placed after the dispenser or even the edge of the dispenser itself, thereby reducing the amount of mouldable adhesive material to be wasted.

In a preferred embodiment, a third component is combined with the laminate of the adhesive and the primary layer together with the release liner as described above.

The third component may be provided in the form of discrete units placed on the release liner with a spacing corresponding to one or more units per each spacing of the mould cavities, said units being pressed into the adhesive layer during the combination.

The third component may comprise two or more materials or webs and may be an adhesive material, a metered amount of an optionally absorbing foam material or a fibrous and/or a non-fibrous porous material.

In a preferred embodiment of the invention the third component is a laminate having a top primary layer at the surface to be pressed into the adhesive layer. A top film stabilises the unit during the combination and renders it possible to press-in units of materials not having the physical dimensional stability to be pressed into the adhesive material.

The invention furthermore relates to a layered product comprising at least two layers where a first layer is constituted by a continuous and deformable sheet, a second layer is constituted by a mouldable material which material comprises a third component in the form of individual units forming part of the surface of the mouldable material facing away from the deformable sheet and the units having at least two layers, at the surface not forming a part of the surface of the mouldable material facing away from the deformable sheet and wherein the mouldable material facing away from the deformable sheet is optionally covered by a release liner.

The first layer may thus be constituted by a non-elastic but deformable carrier layer such as a paper material and an elastic cover layer releasably connected to each other.

In the layered product produced in accordance with the invention, the plastic mouldable material is preferably an adhesive material and the product is preferably a wound dressing or a semi-manufacture in the production of dressings, skin and wound care devices, fastening means for dressings, ostomy equipment, breast prostheses, wound drains or catheters for incontinence equipment, or for use in electrodes for application to the skin.

The first primary layer may typically be a thermoplastic film or a layered combination of two or more materials. The individual layers may, e.g., be one or more different paper materials, polyolefins such as polyethylene, polypropylene or the like, thermoplastic polyurethanes, polyesters, polyamides, polyvinylacetate and the like in the form of films, woven, non woven or knitted materials or other types of films which are mouldable using stress and/or elevated temperatures. The primary layer may, e.g., include a water impervious layer or film of any suitable material known per se for use in the preparation of wound dressings e.g. a foam, a water-impervious non woven layer or a polyurethane, polyethylene, polyester or polyamide film. A suitable material for use as a water impervious film is a polyurethane. A preferred low friction film material is disclosed in U.S. Pat. No. 5,643,187.

The second mouldable material may, e.g., be a skin-friendly adhesive. Such an adhesive may be any skin-friendly adhesive known per se, e.g., an adhesive comprising hydrocolloids or other moisture absorbing constituents for prolonging the time of use. The adhesive may suitably be of the types disclosed in GB Patent Specification No. 1 280 631, in DK Patent Specifications Nos. 127,578, 148,408, 154,806, 147,226 and 154,747, in EP published application Nos. 0 097 846 and 0 415 183, in SE published application No. 365,410, in WO publication No. 88/06894, in U.S. Pat. No. 4,867,748, and in NO published application No. 157, 686. Especially preferred are the adhesives disclosed in U.S. Pat. Nos. 4,367,732 and 5,051,259 and DK Patent Specification No. 169,711.

Suitable hydrocolloids are naturally occurring hydrocolloids such as guar, locust bean gum (LBG), pectin, alginates, gelatine, xanthan or karaya, semisynthetic hydrocolloids such as cellulose derivatives (e.g., salts of carboxymethylcellulose, methylcellulose and hydroxypropylmethylcellulose), sodium starch glycolate and synthetic hydrocolloids such as polyvinylalcohol or polyethylene glycol.

It is advantageous if the dressing according to the invention comprises wound healing associated indicator(s), cushions or similar device for treatment or, prophylaxis of formation of wounds and/or skin abnormalities. This permits a concomitant medical treatment of the wound and an easy and non-contaminating application of the active ingredients, e.g., by incorporating active ingredients such as a cytochine such as growth hormone or a polypeptide growth factor or retinoids giving rise to the incorporation of such active substances in a form being apt to local application in a wound in which the medicament may exercise its effect on the wound, other medicaments such as bacteriostatic or bactericide compounds, e.g., iodine, iodopovidone complexes, chloramine, chlorohexidine, silver salts, zinc or salts thereof, metronidazol, sulpha drugs, and penicillins, tissue-healing enhancing agents, e.g., RGD tripeptides and the like, enzymes for cleansing of wounds, e.g., pepsin, trypsin and the like, cytotoxic agents and proliferation inhibitors for use in for example surgical insertion of the product in cancer tissue and/or other therapeutic agents which optionally may be used for topical application, pain releasing agents, emollients, retinoids or agents having a cooling effect which is also considered an aspect of the invention.

In the present context growth hormone is intended to designate any growth hormone which is applicable in accordance with the invention such as human, bovine, ovine, porcine, equine, salmon or tuna growth hormone or analogues or derivatives thereof such as shortened or extended growth hormones such as methionyl growth hormone. A growth hormone is preferably human growth hormone.

For treatment or prevention of corns or warts it is preferred to include components having cheratolytic effect such as alpha-hydroxy acids or beta-hydroxyacids such as malic acid, citric acid, lactic acid, or salicylic acid and optionally urea and/or glycerol in the dressing, preferably as a part of a third component.

Wound healing associated indicator(s) may e.g., be indicators of pH, partial pressure of $O_2$, temperature, radical mechanisms or biotechnological assays, e.g., indicating formation of collagen.

Release liners which are suitable for use with the dressing of the invention can be made of kraft, paper, polyethylene, polypropylene, polyester or composites of any of these materials. The liners are preferably coated with release agents such as fluorochemicals or silicones. The release liner may, if present, be removed before or during application.

The invention will now be described more in detail by way of an example embodying the process of this invention for the preparation of wound dressings.

Reference is made to the drawing showing a schematic diagram of an apparatus for carrying out the method of the invention. In this embodiment a roller 2 provides a supply of a first layer, a carrier polyurethane film 1, and a continuously rotating roller 3 e.g., made from aluminum is provided with at least one series of mould cavities 4 in the surface along the periphery of the roller. The mould cavities may preferably be exchangeable to provide any desired linear, curved or irregular contour to the final product. A dispenser head 5 having a discharge orifice, from which material for a second layer, a mouldable material in the form of an adhesive of the type disclosed in U.S. Pat. No. 4,367,732 is provided above or in communication with the mould cavities. It is preferred that the mould cavities are essentially horizontal in orientation when in communication with the dispenser, but it is understood that the mouldable material can be added from any suitable angle as gravity often has an almost negligable influence compared to the adhesive property of the mouldable material. Preferably the addition takes place from an angle above the horizontal level of the rotating roller.

The edge of the dispenser head 5 itself can serve as scraper and remove surplus of mouldable material. Also a separate scraper, doctor or roller (not shown in FIG. 1), can be furnished to remove surplus mouldable material e.g. by scraping or rolling.

A third layer, a release liner layer 6, is provided from an essentially continuous supply (not shown). In the embodiment shown, discrete units 8 of a third component are placed on the release liner layer 6 with a spacing corresponding to one or more units per each spacing of the mould cavities and being brought into contact with the first layer on the roller 3 at a laminating and contouring station 9 pressing said units into the adhesive layer during the combination.

After lamination and contouring the individual products may be cut in a later cutting station, preferably in line with the lamination.

When carrying out the process of the invention, a sheet of carrier film 1 is pulled from the supply roller 2 and extended around the continuos rotating roller 3. Some or all of the mould cavities 4 which are covered completely with the carrier film 1 may be subjected to a vacuum if necessary in order to draw the carrier film 1 into the mould cavities. At the same time the roller 3 may be heated to a temperature in consideration of the material used as carrier film 1 which heating causes the film to relaxate fully or partially and to maintain the shape given by the mould cavities. The temperature may also depend on the softening point of the second layer if this is a thermoplastic material which needs to be kept mouldable.

The moulding cavity moves forward with the roller, either stepwise or, preferably continuously, and a metered amount of a thermoplastic material is dispensed thereon. The thermoplastic material may be plasticized and pumped to an intermediate reservoir from which the thermoplastic material is transported to a dispenser placed above or in communication with the moulding cavity. The plastic material is preferably dispensed at a rate corresponding to the volume of the passing mould cavities if no third component is to be pressed into the product, or at a rate corresponding essentially to the volume filling the mould together with the inserted third unit or units of a third component. The distribution into the moulding cavity may be assisted by a pressure performed on the material by the dispenser or by, e.g., a roller or a doctor blade placed after the dispenser. It will be obvious to a person skilled in the art to adjust the distance and the angle between the roller and any type of surplus removing member to obtain an adequate removal and distribution of the thermoplastic material. It is also envisaged that the plastic material may be dispensed in metered amounts corresponding to the load of a mould cavity. The mould cavities preferably constitutes a cutting tool also for cutting the dressings produced into individual dressings in combination with the lamination of the release liner and optionally the third component.

What is claimed is:

1. A method for production of a layered product having at least two layers, a first primary layer and a second layer of mouldable material, comprising the steps of:

providing a continuous supply of a primary layer material to a plurality of moulding cavities arranged in an endless loop;

creating a vacuum between said primary layer material and said moulding cavities to draw the primary layer material into contact with walls of said moulding cavities;

dispensing a metered supply of said mouldable material to said plurality of moulding cavities on said primary layer using a dispenser positioned in communication with said moulding cavities, a surplus of said mouldable material located on an outer surface of said endless loop being distributed with said dispenser into a subsequent molding cavity by scraping; and heating the walls of the moulding cavities to a temperature adequate to relax the material of the first primary layer and to maintain a shape given by the moulding cavities.

2. The method according to claim 1, wherein the second mouldable material is provided as an essentially continuous coating with a varying thickness on the first primary layer.

3. The method according to claim 1, wherein the walls of the moulding cavities are heated to a temperature adequate to keep the mouldable material in a plasticized state.

4. The method according to claim 1, wherein a third component is combined with a laminate of the mouldable material and the primary layer together with a release liner.

5. A method for production of dressings having at least two layers, a first primary layer and a second layer of mouldable adhesive material, said method comprising the steps of:

providing a continuous supply of a primary layer material to a plurality of moulding cavities arranged in an endless loop along a roller surface;

drawing the primary layer material into contact with said plurality of moulding cavities by creating a vacuum between said primary layer material and said moulding cavities;

dispensing a metered amount of said mouldable adhesive material on said primary layer in communication with the moulding cavities and scraping excess mouldable adhesive material from said roller surface into a subsequent moulding cavity;

heating the moulding cavities to a temperature adequate to relax the material of the first primary layer;

laminating a release liner on the mouldable adhesive material and contouring at least one of the primary layer, the release liner, and the second layer of mouldable adhesive material into individual, contoured dressings; and removing the dressings from the moulding cavities.

6. The method according to claim 5, wherein a third component is combined with a laminate of the adhesive material and the primary layer together with the release liner.

7. The method according to claim 6, wherein the third component is provided in the form of discrete units placed on the release liner with a spacing corresponding to one or more units per each spacing of the moulding cavities, said units being pressed into the adhesive layer during the combination.

8. The method according to claim 6, wherein the third component is a laminate having a primary film at the surface to be pressed into the adhesive layer, said third component including at least one of two or more materials selected from the group consisting of webs of an adhesive material, a metered amount of an absorbing foam material, a fibrous porous material and a non-fibrous porous material.

9. A method for producing a layered product with at least a primary layer material and a mouldable layer material, said method comprising the steps of:

applying a continuous supply of said primary layer material to a roller surface having a plurality of spaced moulding cavities therein separated by non-cavity areas having generally cylindrical curved surfaces;

dispensing a metered quantity of said mouldable layer material on top of the primary layer material;

distributing the mouldable layer material and removing surplus mouldable layer material from said non-cavity areas into a subsequent moulding cavity of the roller surface by scraping said non-cavity areas of said roller; and heating said walls of said moulding cavities to a temperature adequate to relax said primary layer material.

10. The method according to claim 5, further comprising the step of separating the dressings into individual dressings.

11. The method according to claim 5, further comprising the step of packing the dressings.

12. The method according to claim 1, wherein said mouldable material is dispensed by said dispenser at a rate corresponding to a volume of said moulding cavities passing by the dispenser.

13. The method according to claim 5, wherein said metered amount of mouldable adhesive material is dispensed by a dispenser in communication with said moulding cavities, at a rate corresponding to a volume of said moulding cavities.

14. The method according to claim 9, wherein said moldable layer material is dispensed by a dispenser in communication with said moulding cavities, at a rate corresponding to a volume of said moulding cavities on said roller surface.

15. The method according to claim 9 wherein, during the step of applying the primary layer material, a vacuum is created between said moulding cavities and said primary layer material to draw said primary layer material into contact with said moulding cavities.

* * * * *